(12) United States Patent
Pawliszyn

(10) Patent No.: US 10,429,362 B2
(45) Date of Patent: Oct. 1, 2019

(54) SYSTEM AND METHOD FOR DESORBING AND DETECTING AN ANALYTE SORBED ON A SOLID PHASE MICROEXTRACTION DEVICE

(71) Applicant: JP SCIENTIFIC LIMITED, Waterloo (CA)

(72) Inventor: Janusz B. Pawliszyn, Waterloo (CA)

(73) Assignee: JP SCIENTIFIC LIMITED, Waterloo (CA)

(*) Notice: Subject to any disclaimer, the term of this patent is extended or adjusted under 35 U.S.C. 154(b) by 0 days.

(21) Appl. No.: 16/162,034

(22) Filed: Oct. 16, 2018

(65) Prior Publication Data

US 2019/0049415 A1 Feb. 14, 2019

Related U.S. Application Data

(63) Continuation-in-part of application No. PCT/CA2017/050562, filed on May 10, 2017.
(Continued)

(51) Int. Cl.
*G01N 30/72* (2006.01)
*G01N 1/40* (2006.01)
(Continued)

(52) U.S. Cl.
CPC ......... *G01N 30/7266* (2013.01); *G01N 1/405* (2013.01); *G01N 1/44* (2013.01);
(Continued)

(58) Field of Classification Search
CPC ......... A61B 10/0045; A61B 5/150358; G01N 1/405; G01N 1/44; G01N 2001/1445;
(Continued)

(56) References Cited

U.S. PATENT DOCUMENTS 4,140,653 A 2/1979 Imura et al.
4,476,231 A 10/1984 Deindoerfer et al.
(Continued)

FOREIGN PATENT DOCUMENTS

CN 2630850 Y 8/2004
CN 102698720 A 10/2012
(Continued)

OTHER PUBLICATIONS

U.S. Appl. No. 11/208,933, Non-final Office Action dated Mar. 27, 2006.
(Continued)

*Primary Examiner* — Jennifer Wecker
(74) *Attorney, Agent, or Firm* — Borden Ladner Gervais LLP; David Nauman

(57) ABSTRACT

Disclosed herein is a system for desorbing and detecting an analyte sorbed on a solid phase microextraction (SPME) device. The system includes a desorption chamber sized to accept the SPME device while defining a void volume of less than about 50 μL; a flow injector in fluid connection with the desorption chamber, the desorption chamber and the flow injector being fluidly connected by at least a flow-insulating fluid connector; a solvent source in fluid connection with the flow injector; and a fluid switch that: in a desorption position, allows the solvent to be sprayed from the flow injector while flow-insulating any desorption solution in the desorption chamber, and in an detecting position, turns off the solvent source while maintaining the fluid connection between the flow injector and the desorption chamber, transferring the desorption solution through the flow-insulating fluid connector to the flow injector as a substantially undiluted plug of liquid.

26 Claims, 7 Drawing Sheets

Related U.S. Application Data

(60) Provisional application No. 62/333,934, filed on May 10, 2016.

(51) Int. Cl.
| | |
|---|---|
| *G01N 27/62* | (2006.01) |
| *H01J 49/04* | (2006.01) |
| *G01N 21/71* | (2006.01) |
| *G01N 1/44* | (2006.01) |
| *G01N 30/00* | (2006.01) |
| G01N 30/06 | (2006.01) |
| G01N 1/14 | (2006.01) |

(52) U.S. Cl.
CPC ......... *G01N 21/714* (2013.01); *G01N 27/622* (2013.01); *G01N 30/00* (2013.01); *H01J 49/0431* (2013.01); G01N 30/06 (2013.01); G01N 2001/1445 (2013.01); G01N 2030/009 (2013.01); G01N 2030/062 (2013.01); G01N 2560/00 (2013.01)

(58) Field of Classification Search
CPC ....... G01N 2030/009; G01N 2030/062; G01N 30/06; G01N 2560/00; G01N 21/714; G01N 27/622; G01N 30/00; G01N 30/7266; H01J 49/165; H01J 49/0431; Y10T 428/2933
See application file for complete search history.

(56) References Cited

U.S. PATENT DOCUMENTS

| | | |
|---|---|---|
| 4,616,652 A | 10/1986 | Simpson |
| 5,047,437 A | 9/1991 | Cooke et al. |
| 5,081,871 A | 1/1992 | Glaser |
| 5,120,510 A | 6/1992 | Gourley et al. |
| 5,424,187 A | 6/1995 | Shor et al. |
| 5,460,813 A | 10/1995 | Leung et al. |
| 5,464,395 A | 11/1995 | Faxon et al. |
| 5,479,923 A | 1/1996 | Rantala |
| 5,640,470 A | 6/1997 | Iyer et al. |
| 5,691,206 A | 11/1997 | Pawliszyn |
| 5,693,228 A | 12/1997 | Koehler et al. |
| 5,808,300 A | 9/1998 | Caprioli |
| 6,027,942 A | 2/2000 | Hutchens et al. |
| 6,042,787 A | 3/2000 | Pawliszyn |
| 6,287,521 B1 | 9/2001 | Quay et al. |
| 6,360,588 B1 | 3/2002 | Ross et al. |
| 6,555,813 B1 | 4/2003 | Beecher et al. |
| 6,558,958 B1 | 5/2003 | Pilevar et al. |
| 6,625,433 B1 | 9/2003 | Poirier et al. |
| 6,651,124 B1 | 11/2003 | McAllister |
| 6,689,603 B2 | 2/2004 | Pompidou et al. |
| 6,730,096 B2 | 5/2004 | Basta et al. |
| 6,743,180 B1 | 6/2004 | Van Bockel |
| 6,808,937 B2 | 10/2004 | Ligler et al. |
| 6,816,607 B2 | 11/2004 | O'Donnell et al. |
| 6,871,556 B2 | 3/2005 | Andresen et al. |
| 7,019,288 B2 | 3/2006 | Becker |
| 7,110,724 B1 | 9/2006 | Epperson et al. |
| 7,125,580 B2 | 10/2006 | Miller et al. |
| 7,151,167 B2 | 12/2006 | Gjerde et al. |
| 7,211,189 B2 * | 5/2007 | Jinno ................. B01J 20/28014 210/198.2 |
| 7,232,689 B2 | 6/2007 | Pawliszyn |
| 7,259,019 B2 | 8/2007 | Pawliszyn et al. |
| 7,384,794 B2 | 6/2008 | Pawliszyn |
| 7,460,589 B2 | 12/2008 | Fujimori et al. |
| 7,468,281 B2 | 12/2008 | Kallury et al. |
| 7,479,390 B2 | 1/2009 | Pawliszyn |
| 7,537,803 B2 | 5/2009 | Wang et al. |
| 7,605,003 B2 | 10/2009 | Chan et al. |
| 7,667,010 B2 | 2/2010 | Gjerde et al. |
| 7,738,605 B2 | 6/2010 | Mobin et al. |
| 8,008,064 B2 | 8/2011 | Pawliszyn et al. |
| 8,080,407 B2 | 12/2011 | Pawliszyn et al. |
| 8,114,660 B2 | 2/2012 | Pawliszyn et al. |
| 8,148,161 B2 | 4/2012 | Higgins et al. |
| 8,206,902 B2 | 6/2012 | Mitani et al. |
| 8,362,219 B2 | 1/2013 | Gjerde et al. |
| 8,364,033 B2 | 1/2013 | Skoog et al. |
| 8,399,055 B2 | 3/2013 | Bakry et al. |
| 8,494,236 B2 | 7/2013 | Jolly et al. |
| 8,538,098 B2 | 9/2013 | Jacob et al. |
| 8,598,325 B2 | 12/2013 | Pawliszyn |
| 8,620,233 B2 | 12/2013 | Brobston |
| 9,108,217 B2 | 8/2015 | Hoerr et al. |
| 9,502,226 B2 | 11/2016 | Brown et al. |
| 2002/0034827 A1 | 3/2002 | Singh et al. |
| 2002/0142745 A1 | 10/2002 | Kang et al. |
| 2003/0135195 A1 | 7/2003 | Jimenez et al. |
| 2003/0180954 A1 | 9/2003 | Riviere et al. |
| 2003/0183758 A1 | 10/2003 | Colburn et al. |
| 2003/0190757 A1 * | 10/2003 | Furuno ................. G01N 30/08 436/178 |
| 2004/0005582 A1 | 1/2004 | Shipwash |
| 2004/0191537 A1 | 9/2004 | Lubda et al. |
| 2004/0224362 A1 | 11/2004 | Gjerde et al. |
| 2004/0241721 A1 | 12/2004 | Gjerde et al. |
| 2005/0032237 A1 | 2/2005 | Sandra et al. |
| 2005/0112650 A1 | 5/2005 | Chang et al. |
| 2005/0118599 A1 * | 6/2005 | Pawliszyn .......... A61B 10/0045 435/6.12 |
| 2005/0133714 A1 | 6/2005 | Vestal et al. |
| 2005/0142033 A1 | 6/2005 | Glezer et al. |
| 2007/0243843 A1 | 10/2007 | Shalash |
| 2008/0023630 A1 | 1/2008 | Boschetti et al. |
| 2008/0193772 A1 | 8/2008 | Agroskin et al. |
| 2008/0242249 A1 | 10/2008 | Gomez et al. |
| 2009/0026122 A1 | 1/2009 | Pawliszyn et al. |
| 2009/0058531 A1 | 3/2009 | Hwang et al. |
| 2009/0190811 A1 | 7/2009 | Zheng et al. |
| 2009/0232369 A1 | 9/2009 | Senegas et al. |
| 2009/0317916 A1 | 12/2009 | Ewing et al. |
| 2010/0130796 A1 | 5/2010 | Combes et al. |
| 2010/0144049 A1 | 6/2010 | Combes et al. |
| 2010/0249591 A1 | 9/2010 | Heimdal et al. |
| 2010/0322496 A1 | 12/2010 | Liu et al. |
| 2012/0004005 A1 | 1/2012 | Ahmed et al. |
| 2012/0078097 A1 | 3/2012 | Wang et al. |
| 2012/0199735 A1 | 8/2012 | Krechmer et al. |
| 2012/0228228 A1 | 9/2012 | Pawliszyn et al. |
| 2013/0051647 A1 | 2/2013 | Miao et al. |
| 2013/0182935 A1 | 7/2013 | Wang et al. |
| 2014/0017693 A1 | 1/2014 | Mao et al. |
| 2014/0040220 A1 | 2/2014 | Kimura et al. |
| 2014/0164715 A1 | 6/2014 | Weiner et al. |
| 2014/0346348 A1 | 11/2014 | Krechmer et al. |
| 2015/0011376 A1 | 1/2015 | Pawliszyn et al. |
| 2015/0068280 A1 | 3/2015 | Ricoul |
| 2015/0231602 A1 | 8/2015 | Pawliszyn |
| 2015/0318158 A1 | 11/2015 | Pawliszyn et al. |
| 2015/0318160 A1 | 11/2015 | Pawliszyn et al. |
| 2015/0364310 A1 | 12/2015 | Musselman |
| 2015/0369712 A1 | 12/2015 | Pawliszyn et al. |

FOREIGN PATENT DOCUMENTS

| | | |
|---|---|---|
| CN | 102847524 A | 1/2013 |
| DE | 19905239 A1 | 8/2000 |
| EP | 1618592 A2 | 1/2006 |
| JP | H1164277 A | 3/1999 |
| JP | 2009539114 A | 11/2009 |
| WO | 9115745 A1 | 10/1991 |
| WO | 0068665 A1 | 11/2000 |
| WO | 03075772 A3 | 9/2003 |
| WO | 2010008450 A2 | 1/2010 |

(56) References Cited

FOREIGN PATENT DOCUMENTS

OTHER PUBLICATIONS

U.S. Appl. No. 11/208,933, Notice of Allowance dated Feb. 20, 2007.
U.S. Appl. No. 11/208,933, Restriction Requirement dated Dec. 1, 2005.
U.S. Appl. No. 11/706,167, Non-final Office Action dated Aug. 2, 2010.
U.S. Appl. No. 11/706,167, Non-final Office Action dated Jan. 21, 2011.
U.S. Appl. No. 11/706,167, Notice of Allowance dated Jun. 16, 2011.
U.S. Appl. No. 11/706,167, Restriction Requirement dated Nov. 17, 2008.
U.S. Appl. No. 12/174,494, Advisory Action dated Mar. 22, 2012.
U.S. Appl. No. 12/174,494, Final Office Action dated Jan. 20, 2012.
U.S. Appl. No. 12/174,494, Non-final Office Action dated Aug. 29, 2011.
U.S. Appl. No. 12/174,494, Non-final Office Action dated Jun. 25, 2014.
U.S. Appl. No. 12/174,494, Restriction Requirement dated Apr. 28, 2011.
U.S. Appl. No. 12/938,876, Non-final Office Action dated Apr. 1, 2011.
U.S. Appl. No. 12/938,876, Notice of Allowance dated Jan. 11, 2012.
U.S. Appl. No. 12/938,876, Notice of Allowance dated Sep. 28, 2011.
U.S. Appl. No. 12/939,360, Non-final Office Action dated Apr. 4, 2011.
U.S. Appl. No. 12/939,360, Notice of Allowance dated Nov. 10, 2011.
U.S. Appl. No. 13/412,122, Final Office Action dated Jul. 25, 2013.
U.S. Appl. No. 13/412,122, Non-final Office Action dated Apr. 8, 2013.
U.S. Appl. No. 13/412,122, Restriction Requirement dated Jan. 22, 2013.
U.S. Appl. No. 13/478,295, Non-final Office Action dated Feb. 11, 2015.
U.S. Appl. No. 13/478,295, Restriction Requirement dated Oct. 9, 2014.
U.S. Appl. No. 14/492,411, Office Action dated Feb. 16, 2016.
U.S. Appl. No. 14/705,238, Office Action dated Sep. 7, 2016.
U.S. Appl. No. 14/705,238, Restriction Requirement dated May 19, 2016.
U.S. Appl. No. 14/738,678, Non-Final Office Action dated Mar. 22, 2017.
U.S. Appl. No. 14/738,678, Restriction Requirement dated Jan. 4, 2017.
U.S. Appl. No. 14/738,688, Notice of Allowance dated Jul. 17, 2017.
U.S. Appl. No. 14/738,688, Notice of Allowance dated Mar. 8, 2017.
U.S. Appl. No. 14/738,688, Office Action dated Nov. 10, 2016.
U.S. Appl. No. 14/839,529, Final Office Action dated Jun. 12, 2017.
U.S. Appl. No. 14/839,529, Notice of Allowance dated Sep. 19, 2017.
U.S. Appl. No. 14/839,529, Office Action dated Jan. 26, 2017.
U.S. Appl. No. 14/839,529, Restriction Requirement dated Oct. 4, 2016.
U.S. Appl. No. 13/412,122, Notice of Allowance dated Sep. 13, 2013.
Vail et al., "Rapid and Unambiguous Identification of Melamine in Contaminated Pet Food Based on Mass Spectrometry with Four Degrees of Confirmation", Journal of Analytical Toxicology, Jul. 2007, vol. 31 (6), pp. 304-312.
Vinas et al., "Method Development and Validation for Strobilurin Fungicides in Baby Foods by Solid-Phase Microextraction Gas Chromatography-Mass Spectrometry," Journal of Chromatography A, Jan. 2009, vol. 1216 (1), pp. 140-146.
Volante et al., "Application of Solid Phase Micro-Extraction (SPME) to the Analysis of Pesticide Residues in Vegetables," Pest Management Science, Jul. 2000, vol. 56 (7), pp. 618-636.
Vuckovic et al., "In Vitro Evaluation of New Biocompatible Coatings for Solid-Phase Microextraction: Implications for Drug Analysis and in Vivo Sampling Applications," Analytica Chimica Acta, Apr. 2009, vol. 638 (2), pp. 175-185.
Wahba, "Spine Interpolation and Smoothing on the Sphere," SIAM Journal on Scientific and Statistical Computing (Society for Industrial and Applied Mathematics), Mar. 1981, vol. 2 (1), pp. 5-16.
Wang et al., "Surface Confined Ionic Liquid as a Stationary Phase for HPLC," The Analyst, Jul. 2006, vol. 131 (9), pp. 1000-1005.
Whang et al., "Solid Phase Microextraction Coupled to Capillary Electrophoresis," Analytical Communications, 1998, vol. 35, pp. 353-356.
Wong et al., "Development and Interlaboratory Validation of a QuEChERS-Based Liquid Chromatography-Tandem Mass Spectrometry Method for Multiresidue Pesticide Analysis," Journal of Agricultural and Food Chemistry, Mar. 2010, vol. 58 (10), pp. 5897-5903.
Yang et al., "Surface Modification and Blood Compatibility of Polyacrylonitrile Membrane with Immobilized Chitosan-Heparin Conjugate," Journal of Polymer Research, Sep. 2002, vol. 9 (3), pp. 201-206.
Zambonin et al., "Solid Phase Microextraction and Gas Chromatography-mass Spectrometry for the Rapid Screening of Triazole Residues in Wine and Strawberries," Journal of Chromatography A, Aug. 2002, vol. 967 (2), pp. 255-260.
Zambonin et al., "Solid Phase Microextraction—Gas Chromatography Mass Spectrometry: A Fast and Simple Screening Method for the Assessment of Organophosphorus Pesticides Residues in Wine and Fruit Juices," Food Chemistry, Jun. 2004, vol. 86 (2), pp. 269-274.
Zeng et al., "An Electrochemically Enhanced Solid-Phase Microextraction Approach Based on a Multi-Walled Carbon Nanotubes/Nafion Composite Coating," Journal of Chromatography A, Jan. 2010, vol. 1217(11), pp. 1735-1741.
Zeng et al., "Determination of Amphetamines in Biological Samples using Electro Enhanced Solid-Phase Microextraction-Gas Chromatography," Journal of Chromatography B, Jul. 2015, vol. 1000, pp. 169-175.
Zeng et al., "Development of Polymethylphenylsiloxane-Coated Fiber for Solid-Phase Microextraction and its Analytical Application of Qualitative and Semi-Quantitative of Organochlorine and Pyrethroid Pesticides in Vegetables," Analytica Chimica Acta, Jun. 2008, vol. 619 (1), pp. 59-66.
Zeng et al., "Ordered Mesoporous Carbon/Nafion as a Versatile and Selective Solid-Phase Microextraction Coating," Journal of Chromatography A, Sep. 2014, vol. 1365, pp. 29-34.
Lambropoulou et al., "Validation of an SPME Method, Using PDMS, PA, PDMS-DVB, and CW-DVB SPME Fiber Coatings, for Analysis of Organophosphorus Insecticides in Natural Waters," Analytical and Bioanalytical Chemistry, Nov. 2002, vol. 374 (5), pp. 932-941.
Lavaud et al., "Optimal Anticoagulation Strategy in Haemodialysis With Heparin-coated Polyacrylonitrile Membrane," Nephrology Dialysis Transplantation, Oct. 2003, vol. 18 (10), pp. 2097-2104.
Lord et al., "Development and Evaluation of a Solid-Phase Microextraction Probe for in Vivo Pharmacokinetic Studies," Analytical Chemistry, Oct. 2003, vol. 75 (19), pp. 5103-5115.
Louch et al., "Dynamics of Organic Compound Extraction from Water Using Liquid-Coated Fused Silica Fibers," Analytical Chemistry, May 1992, vol. 64 (10), pp. 1187-1199.
Martos et al., "Calibration of Solid Phase Microextraction for Air Analyses Based on Physical Chemical Properties of the Coating," Analytical Chemistry, Jan. 1997, vol. 69 (2), pp. 206-215.
Menezes et al., "Development, Validation and Application of a Methodology Based on Solid-Phase Micro Extraction Followed by Gas Chromatography Coupled to Mass Spectrometry (SPME/GC-MS) for the Determination of Pesticide Residues in Mangoes," Talanta, Apr. 2010, vol. 81 (1-2), pp. 346-354.

(56) References Cited

OTHER PUBLICATIONS

Mindrup et al., "Improved Performance of SPME Fibers and Applications," SUPELCO, Sigma-Aldrich Co., 2001, pp. 1-25.

Mirnaghi et al., "Optimization of the Coating Procedure for a High-Throughput 96-Blade Solid Phase Microextraction System Coupled with LC-MS/MS for Analysis of Complex Samples," Analytical Chemistry, Jun. 2011, vol. 83 (15), pp. 6018-6025.

Mirnaghi et al., "Reusable Solid-Phase Microextraction Coating for Direct Immersion whole-Blood Analysis and Extracted Blood Spot Sampling Coupled with Liquid Chromatography-Tandem Mass Spectrometry and Direct Analysis in Real Time-Tandem Mass Spectrometry", Analytical Chemistry, Aug. 2012, vol. 84 (19), pp. 8301-8309.

Moder et al., "Determination of urinary acylcarnitines by ESI-MS coupled with solid-phase microextraction (SPME)", Journal of Mass Spectrometry, Jul. 1997, vol. 32, pp. 1195-1204.

Moneti et al., "Solid-Phase Microextraction of Insect Epicuticular Hydrocarbons for Gas Chromatographic/Mass Spectrometric Analysis," Rapid Communications in Mass Spectrometry, May 1997, vol. 11 (8), pp. 857-862.

Mullett et al., "Direct Determination of Benzodiazepines in Biological Fluids by Restricted-Access Solid-Phase Microextraction," Analytical Chemistry, Mar. 2002, vol. 74 (5), pp. 1081-1087.

Musteata, "Biocompatible Solid Phase Microextraction," Thesis, Master in Science, University of Waterloo, Waterloo, Ontario, Canada, 2006, pp. i-xi and 1-70.

Musteata et al., "Biocompatible Solid-Phase Microextraction Coatings Based on Polyacrylonitrile and Solid-Phase Extraction Phases," Analytical Chemistry, Sep. 2007, vol. 79 (18), pp. 6903-6911.

Namera et al., "Analysis of Anatoxin-A in Aqueous Samples by Solid-phase Microextraction Coupled to High-performance Liquid Chromatography with Fluorescence Detection and On-Fiber Derivatization," Journal of Chromatography A, Jul. 2002, vol. 963 (1-2), pp. 295-302.

Natangelo et al., "Evaluation of Solid Phase Microextraction-Gas Chromatography in the Analysis of Some Pesticides With Different Mass Spectrometric Techniques: Application to Environmental Waters and Food Samples," Analytical Letters, Feb. 2002, vol. 35 (2), pp. 327-338.

Nie et al., "Preparation and Characterization of Polyacrylonitrile-Based Membranes: Effects of Internal Coagulant on Poly (Acrylonitrile-co-maleic Acid) Ultrafiltration Hollow Fiber Membranes," Desalination, Jan. 2004, vol. 160 (1), pp. 43-50.

Oliva et al., "Determination of Chlorpyrifos, Penconazole, Fenarimol, Vinclozolin and Metalaxyl in Grapes, Must and Wine by On-Line Microextraction and Gas Chromatogaphy," Journal of Chromatography A, Feb. 1999, vol. 833 (1), pp. 43-51.

Oliva et al., "Multiresidue Method for the Rapid Determination of Organophosphorus Insecticides in Grapes, Must and Wine," Journal of Chromatography A, Jun. 2000, vol. 882 (1-2), pp. 213-220.

Pawliszyn J., "SPME Method Development" in: Solid Phase Microextraction: Theory and Practice, 1st Edition. New York: Wiley-VCH, 1997, pp. 97-139.

Paya et al., "Analysis of Pesticide Residues Using the Quick Easy Cheap Effective Rugged and Safe (QuEChERS) Pesticide Multiresidue Method in Combination With Gas and Liquid Chromatography and Tandem Mass Spectrometric Detection," Analytical and Bioanalytical Chemistry, Nov. 2007, vol. 389 (6), pp. 1697-1714.

Perez et al., "Transmission-Mode Direct Analysis in Real Time and Desorption Electrospray Ionization Mass Spectrometry of Insecticide-Treated Bednets for Malaria Control," Analyst, Feb. 2010, vol. 135, pp. 712-719.

Poerschmann et al., "Solid Phase Microextraction for Determining the Distribution of Chemicals in Aqueous Matrices," Journal of Analytical Chemistry, Feb. 1997, vol. 69 (4), pp. 597-600.

Reubsaet et al., "Determination of Benzodiazepines in Human Urine and Plasma with Solvent Modified Solid Phase Micro Extraction and Gas Chromatography; Rationalisation of Method Development Using Experimental Design Strategies," Journal of Pharmaceutical and Biomedical Analysis, Dec. 1998, vol. 18 (4-5), pp. 667-680.

Ridgway et al., "Sample Preparation Techniques for the Determination of Trace Residues and Contaminants in Food," Journal of Chromatography A, Jun. 2007, vol. 1153 (1-2), pp. 36-53.

Risticevic et al., "Protocol for Solid-Phase Microextraction Method Development," Nature Protocols, Jan. 2010, vol. 5 (1), pp. 122-139.

Rodriguez-Lafuente et al., "Determination of Cocaine and Methadone in Urine Samples by Thin-Film Solid-Phase Microextraction and Direct Analysis in Real Time (DART) Coupled With Tandem Mass Spectrometry," Analytical and Bioanalytical Chemistry, Dec. 2013, vol. 405 (30), pp. 9723-9727.

Schurek et al., "Application of Head-Space Solid-Phase Microextraction Coupled to Comprehensive Two-dimensional Gas Chromatography-Time-of-Flight Mass Spectrometry for the Determination of Multiple Pesticide Residues in Tea Samples," Analytica Chimica Acta, Mar. 2008, vol. 611 (2), pp. 163-172.

Shirey, "Optimization of Extraction Conditions and Fiber Selection for Semivolatile Analytes Using Solid-Phase Microextraction," Journal of Chromatographic Science, Jul. 2000, vol. 38 (7), pp. 279-288.

Sigma-Aldrich, SPME Sample Prep Made Easy, How to Choose the Proper SPME Fiber, Newsletter, Sigma-Aldrich, Supelco, Supelco Park, Bellefonte, PA 16823-0048, Fall 1999, 4 pages.

Simplicio et al., "Validation of a Solid-Phase Microextraction Method for the Determination of Organophosphorus Pesticides in Fruits and Fruit Juice," Journal of Chromatography A, Feb. 1999, vol. 833 (1), pp. 35-42.

Smith et al., "Solid-Phase Microextraction as a Tool for Studying Volatile Compounds in Frog Skin," Chemistry and Ecology, Dec. 2000, vol. 17 (3), pp. 215-225.

Spottiswoode et al., "Motion-guided segmentation for cine DENSE MRI," Medical Image Analysis, Feb. 2009, vol. 13 (1), pp. 105-115.

Steiniger et al., "Determination of Multiresidue Pesticides in Green Tea by Using a Modified QuEChERS Extraction and Ion-Trap Gas Chromatography/Mass Spectrometry," Journal of AOAC International, Jul. 2010, vol. 93 (4), pp. 1169-1179.

Turiel et al., "Molecularly Imprinted Polymeric Fibers for Solid Phase Microextraction," Analytical Chemistry, Apr. 2007, vol. 79 (8), pp. 3099-3104.

U.S. Appl. No. 15/446,972, Restriction Requirement dated Nov. 2, 2018.

U.S. Appl. No. 10/506,827, Final Office Action dated Dec. 28, 2005.

U.S. Appl. No. 10/506,827, Final Office Action dated Oct. 18, 2007.

U.S. Appl. No. 10/506,827, Final Office Action dated Oct. 26, 2006.

U.S. Appl. No. 10/506,827, Non-final Office Action dated Jun. 30, 2005.

U.S. Appl. No. 10/506,827, Non-final Office Action dated May 29, 2007.

U.S. Appl. No. 10/506,827, Non-final Office Action dated May 30, 2006.

U.S. Appl. No. 10/506,827, Notice of Allowance dated Jan. 30, 2008.

U.S. Appl. No. 11/206,804, Final Office Action dated Jul. 12, 2006.

U.S. Appl. No. 11/206,804, Non-final Office Action dated Jan. 12, 2007.

U.S. Appl. No. 11/206,804, Non-final Office Action dated Jan. 9, 2006.

U.S. Appl. No. 11/206,804, Notice of Allowance dated May 16, 2007.

U.S. Appl. No. 11/206,804, Restriction Requirement dated Oct. 28, 2005.

U.S. Appl. No. 11/208,933, Final Office Action dated Jan. 3, 2007.

U.S. Appl. No. 11/208,933, Non-final Office Action dated Aug. 9, 2006.

Aguinaga et al., "Solid Phase Microextraction Coupled to Gas Chromatography-Mass Spectrometry for the Analysis of Famoxadone in Wines, Fruits and Vegetables," Spectroscopy Letters: An International Journal for Rapid Communication, Dec. 2009, vol. 42 (6-7), pp. 320-326.

(56) References Cited

OTHER PUBLICATIONS

Alpendurada., "Solid-phase Microextraction:A Promising Technique for Sample Preparation in Environmental Analysis," Journal of Chromatography. A, Aug. 2000, vol. 889(1-2), pp. 3-14.
Anastassiades et al., "Fast and Easy Multiresidue Method Employing Acetonitrile Extraction/partitioning and "Dispersive Solid-phase Extraction" for the Determination of Pesticide Residues in Produce," Journal of AOAC International, Mar. 2003, vol. 86 (2), pp. 412-431.
Augusto et al., "New Sorbents for Extraction and Microextraction Techniques," Journal of Chromatography A, Apr. 2010, vol. 1217 (16), pp. 2533-2542.
Banerjee et al., "Validation and Uncertainty Analysis of a Multi-Residue Method for Pesticides in Grapes Using Ethyl Acetate Extraction and Liquid Chromatography—Tandem Mass Spectrometry," Journal of Chromatography A, Nov. 2007, vol. 1173 (1-2), pp. 98-109.
Beltran et al., "Solid-Phase Microextraction in Pesticide Residue Analysis," Journal of Chromatography A, Jul. 2000, vol. 885 (1-2), pp. 389-404.
Bistoquet et al., "Left Ventricular Deformation Recovery From Cine MRI Using an Incompressible Model," IEEE Transactions on Medical Imaging, Sep. 2007, vol. 26 (9), pp. 1136-1153.
Boos et al., "Alkyl-diol Silica (ADS): Restricted Access Precolumn Packing for Direct Injection and Coupled-column Chromatography of Biofluids," Fresenius' Journal of Analytical Chemistry, Jan. 1995, vol. 352 (7), pp. 684-690.
Cai et al., "Vinyl Crown Ether as a Novel Radical Crosslinked Sol-Gel SPME Fiber for Determination of Organophosphorus Pesticides in Food Samples," Analytica Chimica Acta, Feb. 2006, vol. 559 (1), pp. 89-96.
Capobiango et al., "A Solid Phase Microextraction Method for the Chromatographic Determination O Organophosphorous Pesticides in Fish, Water, Potatoes, Guava and Coffee," Journal of Brazilian Chemical Society, Oct. 2005, vol. 16 (5), pp. 907-914.
Charlton et al., "Determination of Imisazole and Triazole Fungicide Residues in Honeybees Using Gas Chromatography-Mass Spectrometry," Journal of Chromatography A, Feb. 2007, vol. 1141 (1), pp. 117-122.
Chen, et al., "High Extraction Efficiency for Polar Aromatic Compounds in Natural Water Samples using Multiwalled Carbon Nanotubes/Nafion Solid-Phase Microextraction Coating," Journal of Chromatography A, Jul. 2009, vol. 1216 (52), pp. 9143-9148.
Chen et al., "Solid Phase Microextraction Coupled to High-Performance Liquid Chromatography," Analytical Chemistry, Aug. 1995, vol. 67 (15), pp. 2530-2533.
Chen et al., "The Application of Solid Phase Microextraction in the Analysis of Organophosphorous Pesticides in a Food Plant," Environmental Science and Technology, Dec. 1998, vol. 32 (23), pp. 3816-3820.
Chipuk et al., "The Influence of Material and Mesh Characteristics on Transmission Mode Desorption Electrospray Ionization," Journal of the American Society for Mass Spectrometry, Apr. 2009, vol. 20 (4), pp. 584-592.
Chipuk et al., "Transmission Mode Desorption Electrospray Ionization," Journal of the American Society for Mass Spectrometry, Nov. 2008, vol. 19 (11), pp. 1612-1620.
Cunha et al., "Fast Low-Pressure Gas Chromatography-mass Spectrometry Method for the Determination of Multiple Pesticides in Grapes, Musts and Wines," Journal of Chromatography A,Jan. 2009, vol. 1216 (1), pp. 119-126.
De Jager et al., "Analysis of Tetramethylene Disulfotetramine in Foods Using Solid- Phase Microextraction-Gas Chromatography-Mass Spectrometry," Journal of Chromatography A, May 2008, vol. 1192 (1), pp. 36-40.
Deng et al., "Strategies for Coupling Solid-Phase Microextraction with Mass Spectometry," Trends in Analytical Chemistry, Mar. 2014, vol. 55, pp. 55-67.

Dietz et al., "Recent Developments in Solid Phase Microextraction Coatings and Related Techniques," Journal of Chromatography A, Jan. 2006, vol. 1103 (2), pp. 183-192.
Djozan et al., "Preparation and Biding Study of Solid Phase Microextraction Fiber on the Basis of Ametryn-Imprinted Polymer—Application to the Selective Extraction of Persistent Triazine Herbicides in Tap Water, Rice, Maize and Onion," Journal of Chromatography A, Mar. 2009, vol. 1216 (12), pp. 2211-2219.
European Patent Application No. 03706179.3, Communication from European Examining Division dated Apr. 29, 2008.
European Patent Application No. 03706179.3, Communication from European Examining Division dated Dec. 17, 2007.
European Patent Application No. 03706179.3, Communication from European Examining Division dated Jan. 24, 2007.
European Patent Application No. 03706179.3, Communication from European Examining Division dated Oct. 23, 2006.
European Patent Application No. 03706179.3, Intention to Grant from European Examining Division dated Aug. 19, 2008.
Frangi et al., "Three-Dimensional Modeling for Functional Analysis of Cardiac Images: A Review," IEEE Transactions on Medical Imaging, Jan. 2001, vol. 20 (1), 24 pages.
Frerot et al., "Solid-Phase Microextraction (SPME): A New Tool in Pheromone Identification in Lepidoptera," Journal of High Resolution Chromatography, Jun. 1997, vol. 20 (6), pp. 340-342.
Furlong et al., "Routine Determination of Sulfonylurea, Imidazolinone, and Sulfonamide Herbicides at Nanogram-Per-Liter Concentrations by Solid-Phase Extraction and Liquid Chromatography/Mass Spectrometry," The Science of the Total Environment, Apr. 2000, vol. 248 (2-3), pp. 135-146.
Fytianos et al., "Solid Phase Microextraction Applied to the Analysis of Organophosphorus Insecticides in Fruits," Chemosphere, Dec. 2006, vol. 65 (11), pp. 2090-2095.
Gomez-Rios et al., "Solid Phase Microextraction (SPME)-Transmission Mode (TM) Pushes Down Detection Limits in Direct Analysis in Real Time (DART)," Chemical Communications, Aug. 2014, vol. 50, pp. 12937-12940.
Gonzalez-Rodriguez et al., "Multiresidue Determination of 11 New Fungicides in Grapes and Wines by Liquid-Liquid Extraction/Clean-Up and Programmable Temperature Vaporization Injection with Analyte Protectants/Gas Chromatography/Ion Trap Mass Spectrometry," Journal of Chromatography A, Aug. 2009, vol. 1216 (32), pp. 6033-6042.
Guillet et al., "Microwave/SPME Method to Quantify Pesticides Residues in Tomato Fruits," Journal of Environmental Science and Health, Part B: Pesticides, Food Contaminents, Jun. 2009, vol. 44 (5), pp. 415-422.
Heinze, "Ultramicroelectrodes in Electrochemistry," Angewandte Chemie International Edition in English, Sep. 1993, vol. 32 (9), pp. 1268-1288.
Hu et al., "Solid Phase Microextraction of Pesticide Residues from Strawberries," Food Additives and Contaminants, Mar. 1999, vol. 16 (3), pp. 111-117.
Hu et al., "Solid-phase Microextraction of Phenol Compounds Using a Fused-Silica Fiber Coated with beta-Cyclodextrin-bonded Silica Particles", Analytical Sciences, Apr. 2004, vol. 20, pp. 667-671.
International Patent Application No. PCT/CA2003/000311, International Search Report dated Oct. 10, 2003.
International Patent Application No. PCT/CA2015/050550, International Preliminary Report on Patentability dated Dec. 22, 2016.
International Patent Application No. PCT/CA2015/050550, International Search Report and Written Opinion dated Aug. 27, 2015.
International Patent Application No. PCT/CA2015/050551, International Preliminary Report on Patentability dated Dec. 22, 2016.
International Patent Application No. PCT/CA2015/050551, International Search Report and Written Opinion dated Aug. 27, 2015.
International Patent Application No. PCT/CA2017/050279, International Search Report and Written Opinion dated May 12, 2017.
International Patent Application No. PCT/CA2017/050562, International Search Report and Written Opinion dated Aug. 18, 2017.
Jackson et al., "Mass Spectrometry for Genotyping: An Emerging Tool for Molecular Medicine," Molecular Medicine Today, Jul. 2000, vol. 6 (7), pp. 271-276.

(56) References Cited

OTHER PUBLICATIONS

Jahnke et al., "Do Complex Matrices Modify the Sorptive Properties of Polydimethylsiloxane (PDMS) for Non-Polar Organic Chemicals," Journal of Chromatography A, Jul. 2010, vol. 1217 (29), pp. 4765-4770.
Japanese Patent Application No. 2017-517155, Office Action dated Nov. 14, 2017—English Translation Available.
Japanese Patent Application No. 574050/2003, Notice of Reasons for Rejection dated Feb. 10, 2009—English Translation.
Kataoka et al., "Applications of Solid-Phase Microextraction in Food Analysis," Journal of Chromatography A, Jun. 2000, vol. 880 (1-2), pp. 35-62.
Kloskowski, et al, "Membrane Solid-phase Microextraction—A New Concept of Sorbent Preparation," Analytical Chemistry, Sep. 2009, vol. 81 (17), pp. 7363-7367.
Lambropoulou et al., "Headspace Solid-Phase Microextraction in Combination with Gas Chromatography-Mass Spectrometry for the Rapid Screening of Organophosphorus Insecticide Residues in Strawberries and Cherries," Journal of Chromatography A, Apr. 2003, vol. 993 (1-2), pp. 197-203.
Zhang et al., "Solid-Phase Microextraction," Analytical Chemistry, Sep. 1994, vol. 66 (17), pp. 844A-853A.

\* cited by examiner

SYSTEM AND METHOD FOR DESORBING AND DETECTING AN ANALYTE SORBED ON A SOLID PHASE MICROEXTRACTION DEVICE

CROSS REFERENCE TO RELATED APPLICATIONS

This application is a continuation-in-part of PCT Application No. CA2017/050562, which was filed on May 10, 2017 and designated the United States, and which claims the benefit of priority of U.S. Provisional Patent Application No. 62/333,934, filed on May 10, 2016. The entirety of each document is incorporated herein by reference.

FIELD

The present disclosure relates to systems and methods for desorbing and detecting an analyte sorbed on a solid phase microextraction device.

BACKGROUND

The following paragraph is not an admission that anything discussed in them is prior art or part of the knowledge of persons skilled in the art.

Solid phase microextraction (SPME) is a sampling technique that uses a sorbent-coated substrate to extract an analyte from a sampling media. In order to detect the analyte sorbed on the sorbent, the SPME device is transferred to the injection port of a separating and/or detecting instrument, such as a mass spectrometer. The analyte is desorbed from the sorbent coating of the SPME device and provided to the separating and/or detecting instrument.

INTRODUCTION

The following part is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Desorption of an analyte sorbed on an SPME device into a detecting instrument is often performed under conditions of constant flow of a carrier stream. For example, desorption into an electrospray ionization-mass spectrometer (ESI-MS) may be performed by constantly flowing a solvent from a solvent source to an electrospray needle, nebulizing the solvent as it flows from the needle, and transferring the components of the nebulized solvent to the mass spectrometer. When an SPME device is placed in the solvent flow, the analyte is desorbed by the solvent and the desorbed analytes are transferred to the mass spectrometer for detection with help of the solvent. Similar techniques are used with other detecting instruments that use a flowing carrier stream to transfer analytes from the SPME device to the detecting instrument.

Some systems and methods that use a continuous flow of solvent to perform the desorption may generate broad extraction chronograms because, for example, the desorption is not instantaneous, some analytes may desorb at a slower rate than other analytes, or analytes may disperse during transport. For example, the SPME device may be positioned in an extraction chamber that inefficiently mixes the desorption solution. In such an extraction chamber, some of the desorbed analytes may be transported to the mass spectrometer in desorption solution that is sucked into solvent flowing past the extraction chamber, while other desorbed analytes may be further from the flowing solvent and must first diffuse through substantially stagnant desorption solution before being sucked into the flowing solvent.

Therefore, there remains a need for a method and system that transfer the desorption solution in a desorption chamber to a flow injector of a detecting instrument as a substantially undiluted plug of liquid.

In one aspect, the present disclosure provides a system for desorbing and detecting an analyte sorbed on a solid phase microextraction (SPME) device. The system includes a desorption chamber sized to accept the SPME device while defining a void volume of less than about 50 µL. The system also includes a flow injector in fluid connection with the desorption chamber. The desorption chamber and the flow injector are fluidly connected by at least a flow-insulating fluid connector. The system includes a solvent source in fluid connection with the flow injector, and a fluid switch. The fluid switch has a desorption position and a detecting position. In the desorption position, the fluid switch allows the solvent to be sprayed from the flow injector while flow-insulating any desorption solution in the desorption chamber. In the detecting position, the fluid switch isolates the solvent source from the flow injector by turning off the solvent flow while maintaining the fluid connection between the flow injector and the desorption chamber so as to transfer desorption solution in the desorption chamber through the flow-insulating fluid connector to the flow injector as a substantially undispersed plug of liquid.

In one particular example of a system according to the present disclosure, the flow-insulating fluid connector is dimensioned to reduce or avoid diffusion of desorption solution from the desorption chamber to the solvent flowing to the flow injector when (a) the fluid switch is in the desorption position, and (b) the solvent flows from the solvent source to the flow injector. For example: the flow-insulating fluid connector may have a smaller cross-section than a cross-section of the desorption chamber, and/or the flow-insulating flow connector may be sufficiently long in comparison to its cross-section that liquid flowing past one end of the fluid connector does not affect liquid at the other end of the fluid connector.

In another particular example of a system according to the present disclosure, the flow-insulating fluid connector may be sized to be fluidly blocked by an accepted SPME device, thereby fluidly isolating the desorption chamber from the flow injector during desorption. This configuration may be used to increase the duty cycle of the system by sequentially empting a plurality of desorption chambers connected to the same solvent flowing system by sequentially unblocking the flow-insulating fluid connector of each desorption chamber.

In another aspect, the present disclosure provides a method for desorbing and detecting an analyte sorbed on a solid phase microextraction (SPME) device. The method includes: desorbing at least some of the analyte from the SPME device into a desorption solution in a desorption chamber where the desorption solution in the desorption chamber is substantially not flowing to a flow injector. The method includes flushing substantially all of the desorption solution in the desorption chamber to the flow injector as a substantially undiluted plug of liquid. The desorption solution is sprayed by the flow injector into a detection device.

In one particular example of a method according to the present disclosure, the desorption chamber is in fluid connection with the flow injector, and the method includes nebulizing a solvent from the flow injector while the analyte is desorbing into the desorption solution in the desorption chamber. The solvent may be nebulized from the flow injector at a rate sufficient to fluidly isolate the desorption solution in the desorption chamber from the solvent being nebulized. The desorption solution in the desorption chamber may be flushed to the flow injector by (a) reducing the flow rate of solvent provided to the flow injector, or (b) fluidly isolating the flow injector from the solvent source, thereby hydrodynamically driving the desorption solution in the desorption chamber to the flow injector by suction generated by a nebulizing gas.

In another particular example of a method according to the present disclosure, the desorption chamber is not in fluid connection with the flow injector while the analyte is desorbing into the desorption solution in the desorption chamber. In such an example, flushing the desorption solution in the desorption chamber to the flow injector includes making a fluid connection between the desorption chamber and the flow injector. The SPME device may be used to break the fluid connection between the desorption chamber and the flow injector while the analyte is desorbing from the SPME device by blocking an aperture fluidly connected to the flow injector. In such a method, making the fluid connection between the desorption chamber and the flow injector may include unsealing the aperture by removing the SPME device. This method may additionally include sequentially empting a plurality of desorption chambers into to the same solvent flowing system by unblocking each the aperature fluidly connected to each flow injector to transfer the desorption solution to the flow injector. Such a method increases the duty cycle and throughput when the desorption of the analytes from the SPME device takes longer than the detection of the analytes.

BRIEF DESCRIPTION OF THE DRAWINGS

Embodiments of the present disclosure will now be described, by way of example only, with reference to the attached Figures.

DETAILED DESCRIPTION

Figure 1:
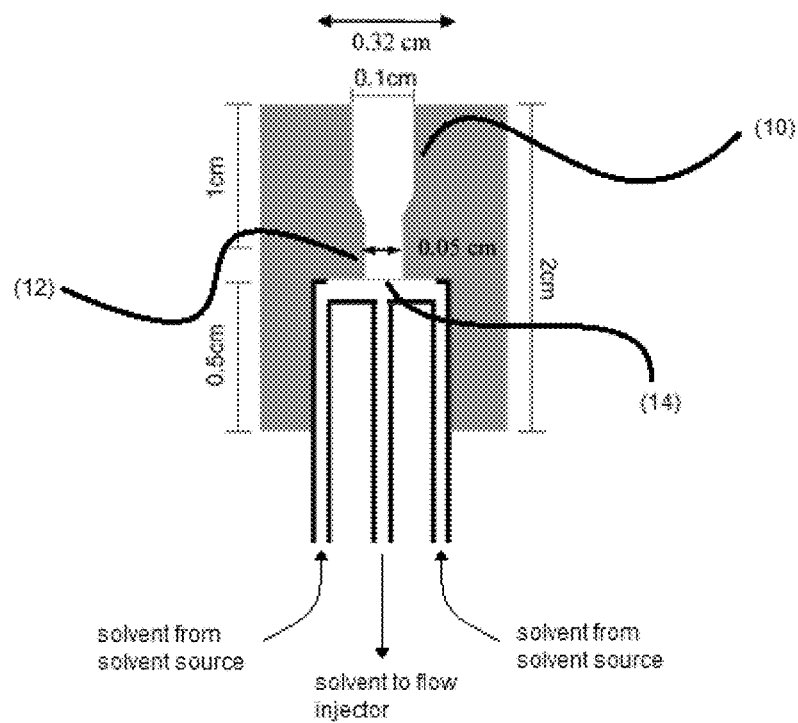
FIG. 1 is a cut-away side view of an exemplary desorption chamber and fluid-isolating flow connector according to the present disclosure.

Generally, the present disclosure provides a system and a method for desorbing and detecting an analyte sorbed on a solid phase microextraction (SPME) device. The system and method transfer the desorption solution in a desorption chamber to a flow injector of a detecting instrument as a substantially undiluted plug of liquid.

The system includes a desorption chamber sized to accept the SPME device while defining a void volume of less than about 50 μL.

The term "void volume" should be understood to refer to the volume available to the desorption solvent when the SPME device is in the desorption chamber. It is desirable to use as small a void volume as possible because smaller void volumes reach equilibrium faster than larger void volumes and, under non-equilibrium desorption times, reducing the void volume can produce for a given desorption time a desorption solution with a more concentrated analyte in comparison to larger void volumes. In some examples, the void volume may be a volume from about 3 to about 50 μL or any volume therebetween, such as 3 μL, 4 μL, 5 μL, 10 μL, 20 μL, 30 μL, 40 μL, or 50 μL.

SPME devices are substrates coated with a solid or liquid extraction phase, which may also be referred to as the "sorbent". The substrate may be, for example, a needle. Exemplary SPME devices are discussed in U.S. Pat. Nos. 7,232,689; 7,259,019; 7,384,794; 7,479,390; 8,008,064; 8,080,407; 8,114,660; and 8,598,325; and in U.S. Patent Publication Nos. US2015/0318158; and US2015/0318160.

The system also includes a flow injector in fluid connection with the desorption chamber. A flow injector would be understood to refer to an injector, such as a needle, that takes a liquid and injects it into a flowing transfer stream, such as a transfer gas. The transfer stream transports the analyte into the detecting instrument. Depending on the detecting instrument, the liquid may ionized and/or at least partially vaporized. In some examples, the flow injector may be a nebulizing needle. In other examples, the flow injector may be an electrospray needle.

The desorption chamber and the flow injector are fluidly connected by at least a flow-insulating fluid connector. The expressions "flow-insulating" should be understood to refer to a fluid connector that is sized and/or shaped to reduce or prevent fluid in the desorption chamber from mixing with fluids flowing in the rest of the system when the analyte is being desorbed from the SPME device. The fluid connector allows the solution in the desorption chamber to flow to the flow injector during the detection step, during which time the desorption solution may mix with fluids outside of the desorption chamber but is preferably transported to the flow injector with minimum mixing with fluids outside of the desorption chamber.

Insulating the desorption solution in the desorption chamber from fluids flowing in the rest of the system during the desorption step allows the concentration of the analyte in the desorption solution to increase over time, such as until an equilibrium concentration is reached. Insulating the desorption solution in the desorption chamber from fluids flowing in the rest of the system during the desorption step may also increase stability in the detection system. In void volumes of less than about 50 μL, where the desorption solution is flow-insulated from fluids in the rest of the system, the analyte may reach an equilibrium concentration in as little as 10 seconds. The time needed to reach equilibrium may be shorted by vibrating the SPME device in the desorption chamber and/or by heating the desorption solvent or the SPME device to increase mass transfer in the system. The terms "insulated" and "isolated" when used to discuss a fluid, solvent, or solution, are equivalent and should be understood to refer to reducing or preventing the fluid, solvent, or solution from mixing with other fluids in the system.

The system also includes a solvent source in fluid connection with the flow injector, and a fluid switch having at least a desorption position and a detecting position. In the desorption position, the fluid switch allows the solvent to be sprayed from the flow injector while flow-insulating any desorption solution in the desorption chamber. In the detecting position, the fluid switch isolates the solvent source from the flow injector by turning-off the solvent flow, while maintaining the fluid connection between the flow injector and the desorption chamber so as to transfer desorption solution in the desorption chamber through the flow-insulating fluid connector to the flow injector as a substantially undiluted plug of liquid.

In the context of the present disclosure, the expression "substantially undiluted plug of liquid" should be understood that at least 90% of the desorption solution in the desorption chamber is transferred to the flow injector in a single volume of fluid, and that the analyte concentration in the plug of fluid once it reaches the flow injector is at least 90% of the analyte concentration in the plug of fluid leaving the desorption chamber.

In one example of a system according to the present disclosure, the flow-insulating fluid connector is dimensioned to reduce or avoid diffusion of desorption solution from the desorption chamber to the solvent flowing to the flow injector when (a) the fluid switch is in the desorption position, and (b) the solvent flows from the solvent source to the flow injector. The flow-insulating fluid connector may have a sufficiently smaller cross-section than a cross-section of the desorption chamber; the length of the flow-insulating flow connector may be sufficiently greater than the cross-section of the flow flow-insulating connector that liquid flowing past one end of the fluid connector does not affect liquid at the other end of the fluid connector; or both. The expressions "sufficiently smaller cross-section" and "length of the flow-insulating flow connector may be sufficiently greater" should be understood to refer to fluid connectors that are dimensioned to prevent or reduce fluid at one end of the fluid connector from interacting with fluid at the other end of the fluid connector. A fluid connector that is sufficiently small in cross-section and/or sufficiently long can reduce or prevent turbulent fluid flow at a first end of the connector from affecting the fluid at a second end of the connector, thereby fluidily isolating the fluid at the second end from fluid at the first end.

In another example of a system according to the present disclosure, the flow-insulating fluid connector is sized to be fluidly blocked by an accepted SPME device. Blocking the fluid connector fluidly isolates the desorption chamber from the flow injector during desorption. Such an exemplary system may also include at least one additional desorption chamber sized to accept an additional SPME device while defining a void volume of less than about 50 µL. The additional desorption chamber may be: connected in parallel to the first desorption chamber through an additional flow-insulating fluid connector that is sized to be fluidly blocked by an additional accepted SPME device. In this manner, this exemplary system can desorb analytes from a plurality of SPME devices, and can inject desorption fluid from one of the SPME devices while the other SPME device(s) are desorbing. A system that includes such a plurality of desorption chambers in parallel may allow the overall throughput to be increased, thereby increasing the duty cycle, even while the time for a single desorption and detection operation is unchanged.

In systems according to the present disclosure, the flow injector may be an electrospray needle, a thermospray nebulizer, a microelectrospray needle, an atmospheric pressure chemical ionization nebulizer, an ion-mobility spectrometry (IMS) nebulizer, an inductively coupled plasma (ICP) nebulizer, or any device that produces a pressure deferential that drives the flow towards the detecting instrument.

The detecting instrument in a system according to the present disclosure may be a mass spectrometer (such as IMS, electrochemical, or spectroscopy based detection) downstream of the flow injector for detecting the desorbed analyte.

Detecting instruments used in a system according to the present disclosure may be operated at a pressure lower than the desorption chamber, which may be at atmospheric pressure. During operation, the flow injector may generate a local low pressure, or the solvent source may have a pressure applied. In either situation, a pressure differential is generated that sucks solvent from the flow injector to the detecting instrument. When the fluid switch is in the desorption position, the solvent being sucked from the flow injector to the detecting instrument is the solvent in the desorption chamber.

A system according to the present disclosure may include a gas source for nebulizing solvent flowing from the flow injector. The gas may be an inert gas. A system may also include an agitator to vibrate an accepted SPME device, a heater to heat the desorption chamber, or both. Agitating the SPME device and heating the desorption fluid in the desorption chamber may increase the rate of analyte desorption.

In particular examples of a system according to the present disclosure, the system includes 3-way junction, such as a chromatographic T-junction, that fluidly connects (1) the desorption chamber, (2) the solvent source, and (3) the flow injector. The desorption chamber is open to the atmosphere, and the flow injector is at a reduced pressure in comparison to the solvent source and the desorption chamber. Having the flow injector at this reduced pressure draws fluid from the solvent source, the desorption chamber, or a mixture of both, as discussed in greater detail below.

The 3-way junction may be arranged in any manner as long as the fluid in the desorption chamber does not drip out, for example when the SPME device is inserted into the desorption chamber. The desorption chamber may be, for example, in a substantially vertical orientation.

The fluid switch is any arrangement that is capable of changing the relative flows of (a) fluid from the solvent source to (b) fluid drawn from the flow injector. For example, when the flow of fluid from the solvent source is greater than the flow of fluid from the flow injector, the additional fluid flows into the desorption chamber; and when the flow of fluid from the solvent source is less than the flow of fluid from the flow injector, fluid in the desorption chamber flows through the flow-insulating 3-way junction to the flow injector. When the fluid flow from the solvent source is substantially identical to the flow of fluid from the flow injector, the amount of fluid in the desorption chamber does not change. In some examples, the fluid switch may be a valve located between the solvent source and the 3-way junction. A substantially undiluted plug of liquid may be delivered to the flow injector by substantially reducing, in a short period of time, the flow of fluid from the solvent source. This may be achieved by, for example, closing a valve located between the solvent source and the 3-way junction. Alternatively, this may be achieved by turning off the flow of solvent at the source.

Exemplary 3-way junctions especially suitable for systems according to the present disclosure may have inner diameters from about 0.01 mm to about 2 mm. Such internal diameters flow insulate the desorption chamber from the flow injector. The desorption chamber may be a portion of tubing that connects to the 3-way junction, where the length of tubing and the internal diameter together define a void volume of less than about 50 µL.

In the context of the present disclosure, a "chromatographic T-junction" should be understood to refer to a connection of tubing that intersects at substantially right angles and that has a dead volume of less than 10 nL. A chromatographic T-junction with a 0.01 mm inner diameter tubing may have a dead volume of about 0.000001 nL. A chromatographic T-junction with a 1 mm inner diameter tubing may have a dead volume of about 1 nL.

In a particular embodiments, the solvent source is connected via the stem portion of the "T", while the desorption chamber and the flow injector are connected via the branch portions of the "T". In this configuration, when the flow rate from the flow injector is identical to the flow rate from the solvent source, the T-junction flow-insulates any desorption solution in the desorption chamber. When the fluid switch is adjusted to substantially reduce the flow rate of solvent from the solvent source relative to the flow rate of solvent from flow injector, such as by stopping the flow of solvent from the solvent source, the desorption solution in the desorption chamber flows through the flow-insulating T-junction to the flow injector as a substantially undiluted plug of liquid. When the fluid switch is adjusted to increase the flow rate of solvent from the solvent source relative to the flow rate of solvent from flow injector, the desorption chamber accepts the additional solvent.

In another aspect, the present disclosure provides a method for desorbing and detecting an analyte sorbed on a solid phase microextraction (SPME) device. The method includes desorbing at least some of the analyte from the SPME device into a desorption solution in a desorption chamber. The desorption solution in the desorption chamber is substantially not flowing to a flow injector during the desorption. The method includes flushing substantially all of the desorption solution in the desorption chamber to the flow injector as a substantially undiluted plug of liquid. The SPME device may be left in the desorption chamber, or may be removed from the desorption chamber. Removing the SPME device may more efficiently empty the desorption chamber. The method also includes spraying the desorption solution through the flow injector into a detection device. The expression "substantially not flowing to a flow injector" should be understood to mean that the desorption solution is fluidly isolated from fluid flowing to the flow injector.

The desorption chamber may be in fluid connection with the flow injector, and the method may include nebulizing a solvent from the flow injector while the analyte is desorbing into the desorption solution in the desorption chamber. The solvent may be nebulized from the flow injector at a rate sufficient to fluidly isolate the desorption solution in the desorption chamber from the solvent being nebulized. Nebulizing the solvent draws fluid from the flow injector. When there is a differential between the flow rate of fluid being drawn from the flow injector and the flow of fluid being provided to the system, fluid may be drawn from the desorption chamber (if the flow rate out of the flow injector is greater) or may be driven into the desorption chamber (if the flow rate into the system is greater) to fill-up the chamber for the next desorption. Further, the flow rate of fluid passing the desorption chamber may affect the mixing of fluid at the entrance of the desorption chamber. In some examples, a fluid velocity of at least about 0.4 cm/s passing by a flow-insulating connector having a sub-microliter volume fluidly isolates the desorption solvent in the desorption chamber. Accordingly, the rate of nebulizing the solvent affects fluid flow into and out of the desorption chamber when the desorption chamber is in fluid connection with the flow injector.

The desorption solution in the desorption chamber may be flushed to the flow injector by (a) reducing the flow rate of solvent provided to the flow injector, or (b) fluidly isolating the flow injector from the solvent source. In either case, the desorption solution in the desorption chamber is hydrodynamically driven to the flow injector by suction generated by the nebulizing gas. The desorption chamber may be refilled by (a) increasing the flow rate of solvent provided to the flow injector in comparison to the flow rate of solvent being nebulized, or (b) decreasing the flow rate of solvent being nebulized in comparison to the flow rate of solvent provided to the flow injector.

In another exemplary method, the desorption chamber is not in fluid connection with the flow injector while the analyte is desorbing into the desorption solution in the desorption chamber, and the method includes flushing the desorption solution in the desorption chamber to the flow injector by making a fluid connection between the desorption chamber and the flow injector. For example, the SPME device can be shaped to facilitate the break in the fluid connection between the desorption chamber and the flow injector while the analyte is desorbing from the SPME device by blocking an aperture fluidly connected to the flow injector. In such a situation, making the fluid connection between the desorption chamber and the flow injector may include unsealing the aperture sealed by the SPME device. The method may include removing the SPME device from the desorption chamber and inserting another SPME device into the desorption chamber to again block the aperture, for example once desorption solvent has been hydrodynamically driven into the desorption chamber. The method may include re-filling the desorption chamber with solvent supplied from the solvent source.

The method may be operated with a plurality of SPME devices being desorbed in parallel. For example, the method may include desorbing, flushing, and spraying an analyte from at least two SPME devices. The desorbed analytes from one of the SPME devices may be flushed to the flow injector and detected by the detecting instrument while the analytes from the other SPME devices are being desorbed in their respective desorption chambers.

The method may include heating the desorption chamber, vibrating the SPME device, or both. Doing so may increase the rate of analyte desorption. Under some conditions, the desorption may be effected for 5 to 20 seconds in order to desorb a sufficient amount of analyte to be detected. In some methods, such as methods that use relatively thicker coatings, the desorption is effected for more than 20 seconds.

Systems and methods according to the present disclosure may have an increased sensitivity, narrower chronogram bands, more reproducible desorption volumes, and/or more reproducible results over systems and methods with desorption chambers that are not fluidly isolated during desorption.

In a system where the desorption chamber is not fluidly isolated during desorption, analyte sorbed on one portion of the SPME coating may take a longer time to travel to the detector than analyte sorbed on another portion of the SPME coating. For example, some desorbed analyte may be transported to the detector by suction flow only, while other desorbed analyte may need to first travel by diffusion before reaching a part of the diffusion chamber where fluid is transported by suction flow to the detector. Since systems and methods according to the present disclosure transport the desorption solvent in substantially a single plug of fluid, the time difference to travel to the detector for analytes at the front of the plug of fluid vs. analytes at the back of the plug of fluid is based only on the volume of the desorption chamber and the flow rate.

Using a desorption chamber with known dimensions where the volume of desorption solvent does not vary over time (since the desorption chamber is fluidly isolated during desorption) may provide a more reproducible desorption volume, which may result in more reproducible desorption results.

Reducing the void volume of the desorption chamber reduces the dilution factor. Desorption chambers according to the present disclosure may have a volume of about 7 μL and a void volume of about 4 μL when the SPME fiber occupies 3 μL, while the total volume of a conventional open port probe (OPP) (i.e. volume of the gap and dome) over a 5 second desorption period is 30-40 μL.

One example of a desorption chamber and flow-insulating flow connector that may be used in a system according to the present disclosure is illustrated in FIG. 1. The desorption chamber (10) is fluidly connected to the flow injector (not illustrated) through the flow-insulating flow connector (12). Fluid travels as noted by the arrows from the solvent source, past the aperture (14) of the flow connecter (12) without significantly disturbing solvent in the desorption chamber (10), and to the flow injector. The dimensions of one specific example are shown in FIG. 1, but it should be understood that these are exemplary only and that the size and shape of the desorption chamber and/or fluid connector may be varied in view of the discussion above.

Figure 2:
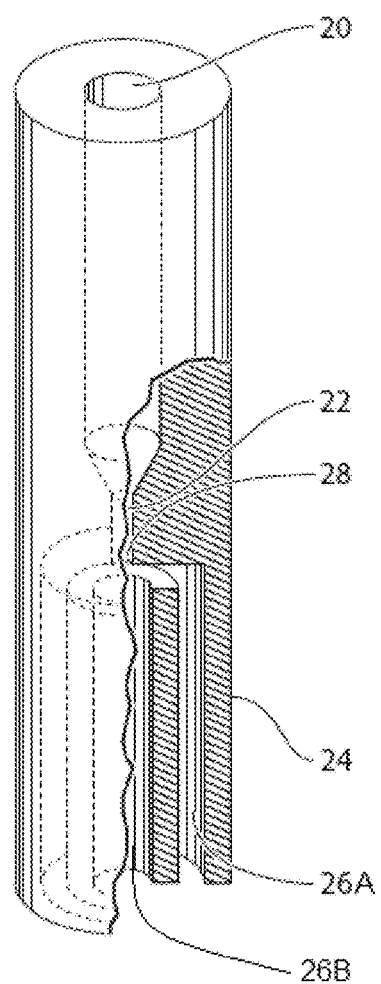
FIG. 2 is a three-quarter view of an exemplary desorption chamber and fluid-isolating flow connector according to the present disclosure.

Another example of a desorption chamber and flow-insulating flow connector that may be used in a system according to the present disclosure is illustrated in FIG. 2. The desorption chamber (20) is fluidly connected to the flow injector (not illustrated) through the flow-insulating flow connector (22). Fluid travels up base (24) through an inflow passage (26A) and past the aperture (28) of the flow connecter (22) without significantly disturbing solvent in the desorption chamber (20), and then down to the flow injector through an outflow passage (26B). The inflow passage (26A) and the outflow passage (26B) are fluidly connected and may be formed though the nesting of concentric cylinders, with the inflow passage (26A) defined by the space between the two cylinders and the outflow passage (26B) defined by the interior space of inner cylinder. The flow-insulating connector (22) illustrated in FIG. 2 has a volume of about 0.25 μL, and the desorption chamber (20) illustrated in FIG. 2 has a volume of about 7 μL.

Figure 3:
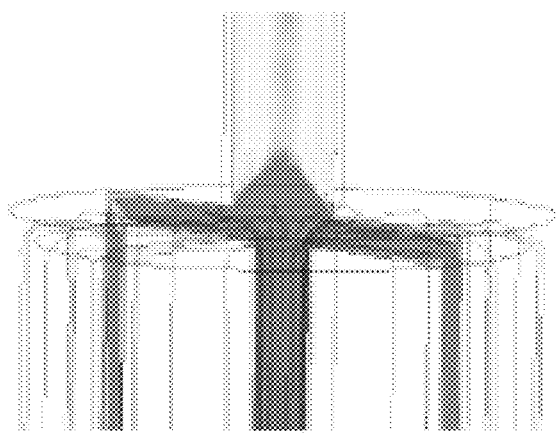
FIG. 3 is an illustration of flow rates in a slice of the fluid-isolating flow connector illustrated in FIG. 2.

The fluid velocity of solvent in the passages and the flow connector of FIG. 2 under steady state conditions is illustrated in FIG. 3 where darker colours represent faster fluid velocity and lighter colours represent slower fluid velocity. The flow profile calculated to generate FIG. 3 was based on a two-dimensional version of the embodiment illustrated in FIG. 2. The fluid velocity in the darkest portions of FIG. 3 represents a velocity of about 0.4 cm/s, while the fluid velocity in the lightest portions represents a velocity of about 0.05 cm/s. Regulating the suction conditions, such as generated by the Venturi effect at the flow injector, and the pump flow conditions allows the fluid flowing through the passages to reach an equilibrium state in which a constant rate of fluid is injected by the flow injector while, at the same time, a stagnant volume of fluid is achieved in the desorption chamber. This is evidenced by the flow lines and velocity gradients shown in FIG. 3 which shows that an SPME fiber can be placed in the desorption chamber without interfering in the electrospray process.

Figure 4:
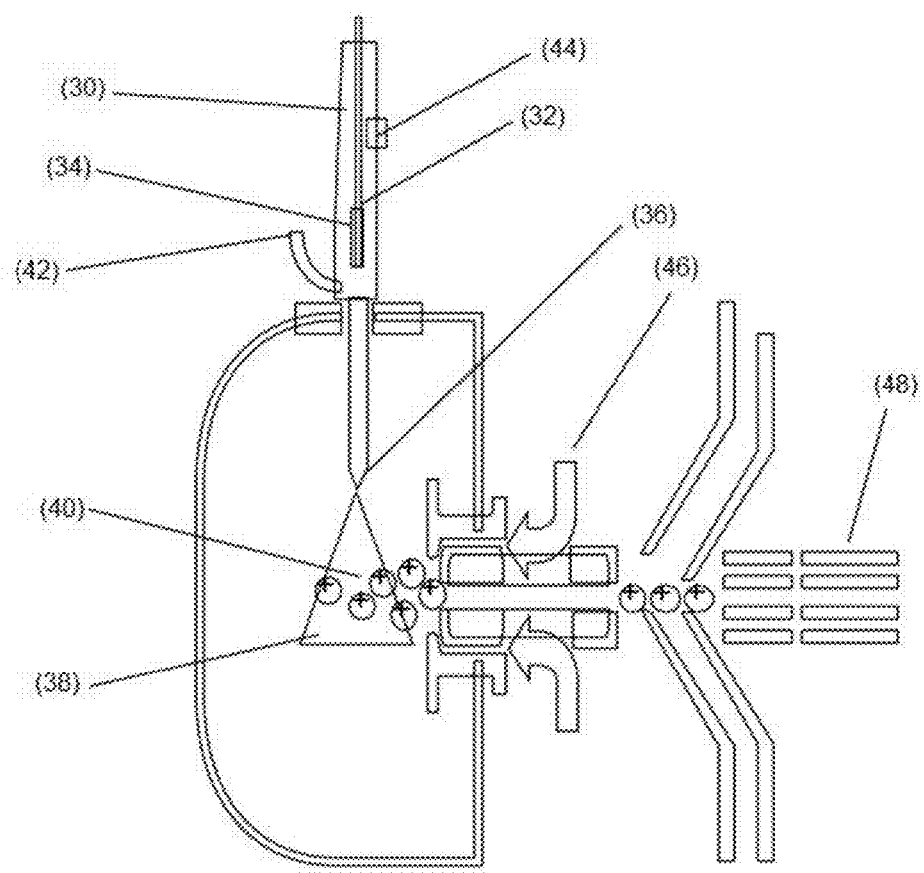
FIG. 4 is a schematic illustration of an exemplary system according to the present disclosure.

A schematic illustration of a system according to the present disclosure is shown in FIG. 4. The desorption chamber (30) is illustrated as having an SPME fiber (32) inserted into the chamber. The SPME fiber has an extraction coating (34). The desorption chamber (30) is fluidly connected to an electrospray needle (36). The electrospray needle produces an electrospray cone (38) of charged components (40) from the solvent. The desorption chamber is also fluidly connected to a tube or passage (42) that can provide solvent to the desorbtion chamber by increasing the fluid flow rate from the tube (42) in comparison to the flow generated by the electrospray needle (36). The chamber also includes an optional fluid sensor (44) that may be used to automatically stop the filling of the desorption chamber. FIG. 4 also illustrates the flow of a drying gas (46) and a mass spectrometer (48) as a detector for the electrosprayed charged components (40).

Figure 5:
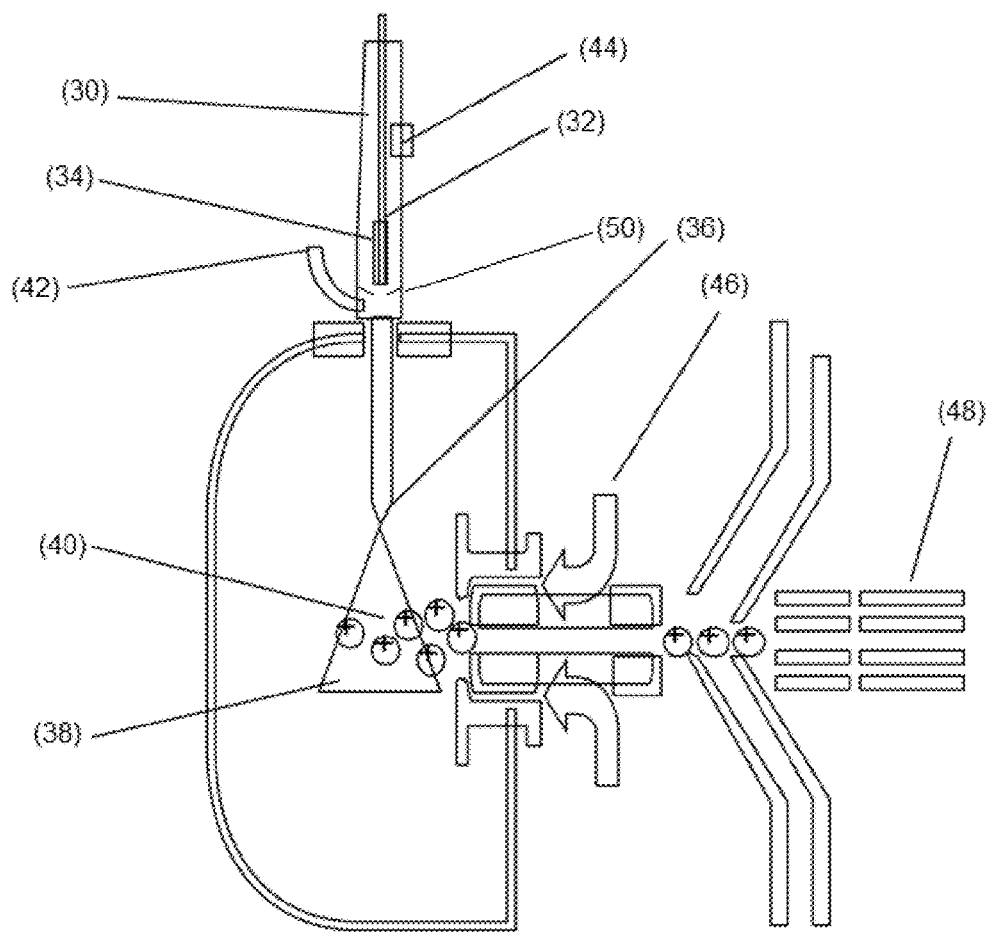
FIG. 5 is a schematic illustration of an exemplary system according to the present disclosure.
Figure 6:
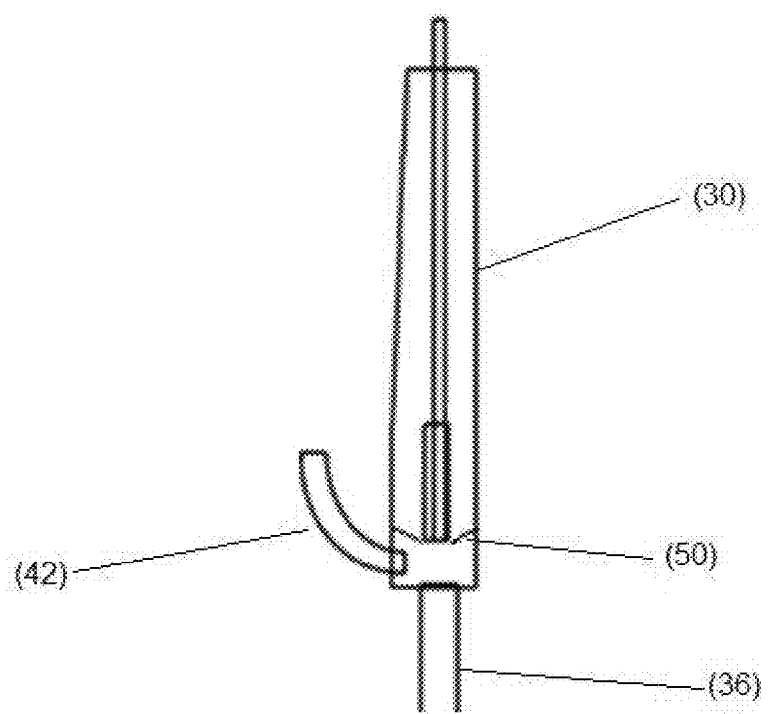
FIG. 6 is an illustration of an exemplary desorption chamber and fluid-isolating flow connector according to the present disclosure.

FIG. 5 shows a schematic illustration of a system similar to the system illustrated in FIG. 4 and, accordingly, the reference numerals are unchanged. However, the system of FIG. 5 additionally includes a narrowed orifice (50) that better fluidly isolates the desorption chamber (30) from the flow of fluid travelling to the electrospray needle (36). In some examples, the orifice (50) may be closed or blocked by the insertion of a SPME device, as illustrated in FIG. 6 which shows the desorption chamber (30), part of the electrospray needle (36), and the orifice (50). In this illustration, the SPME device is moved so that it blocks the orifice (50), thereby preventing or reducing a flow of desorption solvent into the electrospray needle (36) even while fluid flows through the tube or passage (42). Movement of the SPME device away from the orifice (50) opens the desorption chamber and desorption solution can flow to the electrospray needle. The flow of desorption solution to the electrospray needle may be increased by reducing or stopping the flow of fluid from the tube or passage (42).

EXAMPLE

LC-MS grade methanol (MeOH), acetonitrile (ACN), water and isopropanol (IPA) were provided by Fisher Scientific. Codeine, cocaine, buprenorphine, clenbuterol, sertraline, oxycodone and salbutamol were purchased from Sigma Aldrich (Oakville, ON, Canada). The fibers evaluated for extractions were manufactured using an in-house procedure. The coatings used were a mixture of HLB (hydrophilic and lipophilic balance) 5 μm particles and polyacrylonitrile (PAN) prepared by painting the SPME surface with a dispersion of HLB particles (10% by weight) in acrylonitrile monomer, followed by polymerization at 150° C. The fibers were coated having a coating thickness of 20 μm and a length of 4 mm. The experiments were carried out in a triple quadrupole API-4000 from SCIEX.

A desorption chamber as illustrated in FIG. 1 was used, and may be referred to as a modified open port probe (OPP). The desorption chamber was machined from Teflon for its chemical inertness. The desorption chamber includes a hole of 1 mm diameter and 1 cm length that has an approximate volume of 7 μL. The desorption chamber is connected to a flow restriction 0.5 mm in diameter, which generates an additional back pressure to the pump flow. The space between the fitting of the modified OPP and the desorption chamber was minimized (less than 1 mm) in order to reduce the dwell volumes. The system was connected to a 6-port valve in order to bypass the pump flow and produce an efficient flush of the chamber.

The ESI-MS flow conditions of the nebulizer gases (Nitrogen) in the modified open port probe (OPP) were: 90 PSI for gas 1, 70 PSI for gas 2, and 20 PSI for curtain gas 20 PSI. The electrospray voltage was 5500 V.

The MS/MS transitions monitored are shown in Table 1:

TABLE 1

MS/MS transitions and collision energies employed

| Compound | Precursor (m/z) | Product (m/z) | Collision Energy (V) |
|---|---|---|---|
| Oxycodone | 316.098 | 241.054 | 27 |
| Clenbuterol | 276.971 | 202.995 | 16 |
| Salbutamol | 240.071 | 148.071 | 18 |
| Codeine | 300.385 | 165.054 | 39 |
| Cocaine | 304.089 | 182.093 | 18 |
| Sertraline | 306.356 | 159.000 | 26 |
| Buprenorphine | 468.250 | 396.111 | 38 |

The modified OPP was tested using a standard solution of 50 ng/mL of each compound in phosphate buffer solution (PBS). The compounds were extracted using an SPME fiber from a 300 μL of sample for 10 minutes at 1500 rpm. The compounds were desorbed for 5 seconds by placing the SPME fiber in the desorption chamber. After this time, the SPME fiber was taken out from the chamber and the valve was switched to the flushing position for 3 seconds. In the flushing position, methanol from a solvent source is not traveling past the desorption chamber and is instead being actively pumped into the waste. In the flushing position, the only hydrodynamic driven force on the fluid in the desorption chamber is the Venturi suction due to the electrospray. In this manner, a plug of approximate 7 μL is directly injected in to the mass spectrometer with no further dilution. The desorption chamber is refilled by decreasing the Venturi suction for 3 seconds, which can be achieved by reducing the gas 1 pressure from 90 to 80 PSI and switching the valve to the desorption position. Finally, the chamber was ready to use for further experiments.

Figure 7:
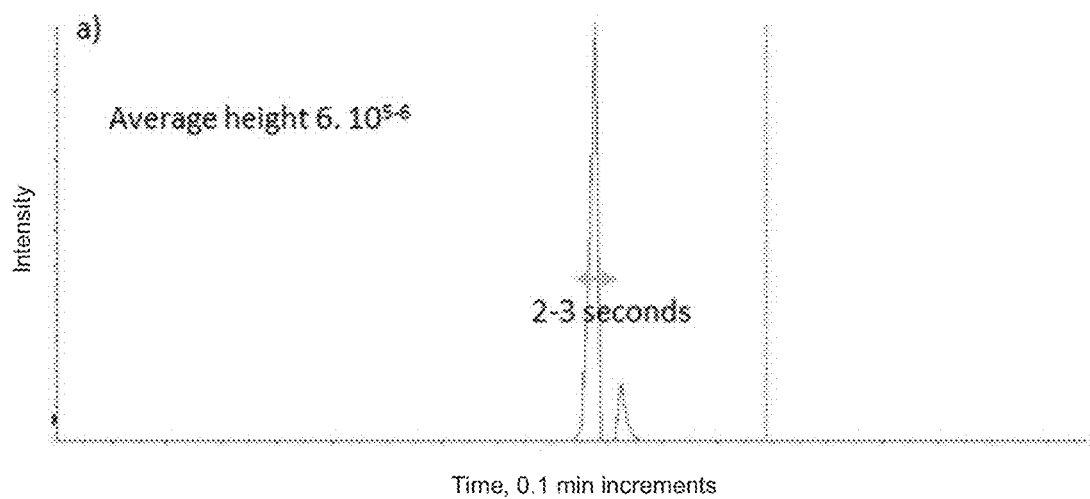
FIG. 7 is an ion chronograph of cocaine extracted and detected using a system and method according to the present disclosure.
Figure 8:
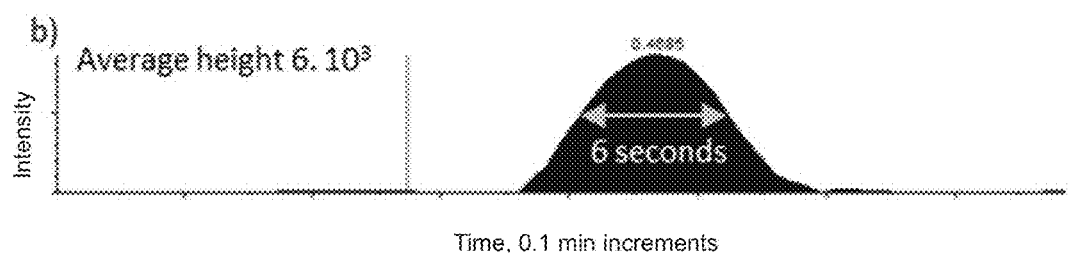
FIG. 8 is an ion chronograph of cocaine extracted and detected using a conventional system and method.

The ion chronograph of cocaine extracted and detected using the method and system described above is shown in FIG. 7, while the ion chronograph of cocaine extracted and detected using a conventional open port probe is shown in FIG. 8. The peak profile in FIG. 7 is very sharp, having a FWHM of 2-3 seconds. In contrast, the peak profile in FIG. 8 is less sharp, having a FWHW of 6 seconds. This corresponds to an increase in sensitivity of between 1 and 2 orders of magnitude.

The length of desorption time was evaluated. Desorption times of 5 and 10 seconds were evaluated. The peak heights, standard deviations, and relative standard deviation (% RSD) are shown in Table 2 for four replicate extractions and desorptions. A desorption time of 10 seconds showed better recovered areas, but the improvements were not significant for the tested compounds. Longer desorption times may be used, for example when desorbing a compound with low kinetics of desorption, or when desorbing from an SPME device with a thick coating.

TABLE 2

| | desorption time | | | | | |
|---|---|---|---|---|---|---|
| | 5 s | | | 10 s | | |
| | Peak height | Std. dev. | % RSD | peak height | Std. dev. | % RSD |
| buprenorphine | 6760 | 1527 | 23 | 2520 | 410 | 16 |
| clenbuterol | 551 | 154 | 28 | 641 | 21 | 3 |
| cocaine | 61733 | 14468 | 23 | 196475 | 63640 | 32 |
| codeine | 197500 | 19092 | 10 | 144000 | 31225 | 22 |
| sertraline | 13400 | 2252 | 17 | 23333 | 4994 | 21 |
| fentanyl | 19900 | 2914 | 15 | 37467 | 15205 | 41 |
| oxycodone | 85050 | 20577 | 24 | 39660 | 6437 | 16 |

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A system for desorbing and detecting an analyte sorbed on a solid phase microextraction (SPME) device, the system comprising:
   a desorption chamber configured to be open to atmospheric pressure during operation and sized to accept the SPME device while defining a void volume of less than about 50 μL;
   a flow injector in fluid connection with the desorption chamber, the desorption chamber and the flow injector being fluidly connected by at least a flow-insulating fluid connector;
   a solvent source in fluid connection with the flow injector; and
   a fluid switch that:
   (a) in a desorption position, is configured to allow the solvent to be sprayed from the flow injector while flow-insulating any desorption solution in the desorption chamber, and
   (b) in an detecting position, is configured to isolate the solvent source from the flow injector by turning off the solvent flow while maintaining the fluid connection between the flow injector and the desorption chamber so as to transfer desorption solution in the desorption chamber through the flow-insulating fluid connector to the flow injector as a substantially undiluted plug of liquid.

2. The system according to claim 1, wherein the flow-insulating fluid connector is dimensioned to reduce or avoid diffusion of desorption solution from the desorption chamber to the solvent flowing to the flow injector when (a) the fluid switch is in the desorption position, and (b) the solvent flows from the solvent source to the flow injector.

3. The system according to claim 2, wherein: the flow-insulating fluid connector has a smaller cross-section than a cross-section of the desorption chamber; the length of the flow-insulating flow connector is sufficiently greater than the cross-section of the flow flow-insulating connector that liquid flowing past one end of the fluid connector does not affect liquid at the other end of the fluid connector; or both.

4. The system according to claim 1, wherein the flow-insulating fluid connector is sized to be fluidly blocked by an accepted SPME device, fluidly isolating the desorption chamber from the flow injector during desorption.

5. The system according to claim 4, further comprising at least one additional desorption chamber sized to accept the SPME device while defining a void volume of less than about 50 µL, wherein the additional desorption chamber: is connected in parallel to the other desorption chamber, is fluidly connected to an additional flow-insulating fluid connector that is sized to be fluidly blocked by an additional accepted SPME device, and is fluidly connected to the flow injector when the additional SPME device is not fluidly blocking the additional flow-insulating fluid connector.

6. The system according to claim 1, wherein the system includes a detection device at a lower pressure than the desorption chamber, and the flow injector is an electrospray needle, a thermospray nebulizer, a microelectrospray needle, an atmospheric pressure chemical ionization nebulizer, an ion-mobility spectrometry nebulizer, an inductively coupled plasma nebulizer, or a system that produces a pressure deferential that drives the solvent flow towards the detection device.

7. The system according to claim 6 wherein the detection device is a mass spectrometer, ion mobility spectrometer, or electrochemical or optical spectroscopy-based detector downstream of the flow injector for detecting the desorbed analyte.

8. The system according to claim 1, wherein the solvent source is fluidly connected with the flow injector at least through a pump capable of applying a pressure to the solvent to transfer the solvent to the flow injector.

9. The system according to claim 1, further comprising a gas source for nebulizing solvent flowing from the flow injector.

10. The system according to claim 1, further comprising an agitator to vibrate an accepted SPME device, a heater to heat the desorption chamber, or both.

11. A system for desorbing and detecting an analyte sorbed on a solid phase microextraction (SPME) device, the system comprising:
 a desorption chamber sized to accept the SPME device while defining a void volume of less than about 50 µL;
 a flow injector in fluid connection with the desorption chamber, the desorption chamber and the flow injector being fluidly connected by at least a flow-insulating fluid connector;
 a solvent source in fluid connection with the flow injector;
 a 3-way junction fluidly connecting (1) the desorption chamber, (2) the solvent source, and (3) the flow injector; and
 a fluid switch that:
  (a) in a desorption position, allows the solvent to be sprayed from the flow injector while flow-insulating any desorption solution in the desorption chamber, and
  (b) in an detecting position, isolates the solvent source from the flow injector by turning off the solvent flow while maintaining the fluid connection between the flow injector and the desorption chamber so as to transfer desorption solution in the desorption chamber through the flow-insulating fluid connector to the flow injector as a substantially undiluted plug of liquid;
 wherein, during operation, the desorption chamber is configured to be open to atmospheric pressure and the flow injector is at a reduced pressure in comparison to the solvent source and the desorption chamber;
 wherein, during operation, the desorption chamber is arranged to reduce or prevent fluid from dripping out of the desorption chamber; and
 wherein the fluid switch is configured to change the relative flows of (a) fluid from the solvent source to (b) fluid drawn from the flow injector.

12. The system according to claim 11, wherein:
 (a) the 3-way junction flow-insulates the desorption solution in the desorption chamber when the fluid switch is set to allow substantially the same flow rate from the solvent source as the flow rate from the flow injector,
 (b) the 3-way junction allows the transfer of the desorption solution in the desorption chamber to the flow injector when the fluid switch is set to allow a reduced flow rate from the solvent source than the flow rate from the flow injector, and
 (c) the 3-way junction allows the transfer of the desorption solution in the desorption chamber to the flow injector when the fluid switch is set to allow an greater flow rate from the solvent source than the flow rate from the flow injector.

13. The system according to claim 11, wherein the desorption chamber is a portion of tubing connected to the 3-way junction.

14. The system according to claim 11, wherein the 3-way junction is a chromatographic T-junction.

15. The system according to claim 11, wherein the fluid switch is a valve fluidly located between the solvent source and the 3-way junction.

16. A method for desorbing and detecting an analyte sorbed on a solid phase microextraction (SPME) device, the method comprising:
 desorbing at least some of the analyte from the SPME device into a desorption solution in a desorption chamber that is in fluid connection with a flow injector, wherein the desorption solution in the desorption chamber is substantially not flowing to the flow injector;
 nebulizing a solvent from the flow injector while the analyte is desorbing into the desorption solution in the desorption chamber, wherein the solvent is nebulized from the flow injector at a rate sufficient to fluidly isolate the desorption solution in the desorption chamber from the solvent being nebulized;
 flushing substantially all of the desorption solution in the desorption chamber to the flow injector as a substantially undiluted plug of liquid; and
 spraying the desorption solution through the flow injector into a detection device.

17. The method according to claim 16, further comprising applying pressure to the solvent using a pump to transfer the solvent from a solvent source to the flow injector.

18. The method according to claim 16, wherein the desorption solution in the desorption chamber is flushed to the flow injector by (a) reducing the flow rate of solvent provided to the flow injector, or (b) fluidly isolating the flow injector from the solvent source, thereby hydrodynamically driving the desorption solution in the desorption chamber to the flow injector by suction generated by a nebulizing gas.

19. The method according to claim 18, further comprising refilling the desorption chamber by increasing the flow rate of solvent provided to the flow injector in comparison to the flow rate of solvent being nebulized, or decreasing the flow rate of solvent being nebulized in comparison to the flow rate of solvent provided to the flow injector.

20. The method according to claim 16, wherein the desorption chamber is not in fluid connection with the flow injector while the analyte is desorbing into the desorption solution in the desorption chamber, and flushing the desorption solution in the desorption chamber to the flow injector comprises making a fluid connection between the desorption chamber and the flow injector.

21. The method according to claim 20, wherein the SPME device breaks the fluid connection between the desorption chamber and the flow injector while the analyte is desorbing from the SPME device by blocking an aperture fluidly connected to the flow injector, and making the fluid connection between the desorption chamber and the flow injector comprises unsealing the aperture.

22. The method according to claim 21, further comprising removing the SPME device from the desorption chamber and inserting another SPME device into the desorption chamber to block the aperture.

23. The method according to claim 20, further comprising desorbing, flushing, and spraying an analyte from at least one additional SPME device, wherein the desorbing of the analytes from the SPME device and from the at least one additional SPME device is performed in parallel.

24. The method according to claim 16, wherein the flow injector is an electrospray needle, a thermospray nebulizer, a microelectrospray needle, an atmospheric pressure chemical ionization nebulizer, an ion-mobility spectrometry nebulizer, an inductively coupled plasma nebulizer, or a system that produces a pressure deferential that drives the solvent flow towards the detection device.

25. The method according to claim 16, wherein the detection device is a mass spectrometer, an ion mobility spectrometer, or an electrochemical or optical spectroscopy-based detector.

26. The method according to claim 16, further comprising heating the desorption chamber, vibrating the SPME device, or both.

* * * * *